United States Patent [19]

Soares

[11] 4,036,823
[45] July 19, 1977

[54] BARBITURIC ACID ANTIGENIC CONJUGATES, THEIR PREPARATION, ANTIBODIES AND USE

[75] Inventor: James R. Soares, Santa Monica, Calif.

[73] Assignee: Biological Developments, Inc., Encino, Calif.

[21] Appl. No.: 571,974

[22] Filed: Apr. 28, 1975

[51] Int. Cl.² .............................................. C07G 7/00
[52] U.S. Cl. .............................. 260/112 R; 23/230 B; 424/1; 424/12; 424/254
[58] Field of Search ........... 260/112 R, 112 B, 209 R; 424/254

[56] References Cited

U.S. PATENT DOCUMENTS

| | | | |
|---|---|---|---|
| 3,766,162 | 10/1973 | Spector | 260/112 B |
| 3,995,021 | 11/1976 | Gross | 260/112 R |

*Primary Examiner*—Paul R. Michl
*Attorney, Agent, or Firm*—McAulay, Fields, Fisher & Goldstein

[57] ABSTRACT

Antigenic barbituric acid conjugates are produced by coupling the hapten acid through its 3-position to an immunogenic carrier. The antigens thus produced can be used to raise antibodies in animals, the antibodies being specific to the barbituric acid hapten compound employed. The antibodies are useful in assaying for the barbituric acid hapten compounds.

25 Claims, No Drawings

BARBITURIC ACID ANTIGENIC CONJUGATES, THEIR PREPARATION, ANTIBODIES AND USE

BACKGROUND OF THE INVENTION

1. Field of the Invention

This invention relates to immunochemicalassaying. Immunochemicalassays are proving of immense value in medicine and biology for the assaying of liquid samples, especially for example, body fluid samples such as blood or urine because of the sensitivity and specificity of such assays. The present invention is particularly concerned with assaying for barbituric acid compounds. Accurate assay of these substances is of the utmost value in medicinal diagnosis and control of drug abuse.

In immunoassaying procedures, for a given a target compound, a synthetic antigen is generally first prepared. Heretofore, this has usually been accomplished by coupling the target compound, through a coupling group to a carrier which confers antigenicity to the entire compound. The compound coupled to the carrier is usually known as a hapten and, when coupled, it functions as an antigenic determinant so that the antibodies produced will bind with the hapten. Thus, the antibodies produced should have a distinct and unique character, such that they will bind with only a specific compound or class of compounds. The objective in devising the synthetic hapten-carrier conjugate is to provide a compound which will generate antibodies that are specific to the target compound.

Antibodies are prepared by injecting the synthetic hapten-carrier conjugate into animals and recovering blood serum from the animals after they have had time to generate antibodies. Typical animals are rabbits and goats.

The principal problem is usually that of synthesizing antigens that are capable of producing sufficiently specific antibodies. Biological fluids such as blood and urine frequently contain very closely related compounds and it is common for antibodies to be unable to distinguish the target compound from close relatives, or sometimes even from distant ones. The antibody is then considered to be a poor one and is said to have low specificity and high cross-reactivity.

The assay itself is commonly a competitive binding assay. In a useful embodiment of such an assay, the target compound, which is not necessarily extracted, is allowed to compete with known quantities of a labeled standard to bind with a known quantity of specific antibody. From measurement of the proportion of the labeling in the standard-antibody complex that results, the amount of target compound present can be calculated. Radioactive labeling is particularly convenient. Fluorescence perturbation and electron spin resonance have been used in the art. Normally it is necessary to remove any unreacted labeled standard, before making the determination on the antibody complex, although theoretically, the determination could be made on the removed unreacted portion of the standard.

THE PRIOR ART

Some 30 years ago, synthetic antigens were prepared by chemically coupling haptens to protein carriers. The antigens were administered to animals with a view to producing antibodies that would bind with the haptens. In the early days, the objective was merely to show binding. More recently the objective has been specificity of the antibody which is the quality of binding selectively with the desired compound and not with others.

Over the years there has been much research into different coupling methods and many synthetic antigens of this type have bween proposed, described and prepared.

Coupling can proceed via the intermediary of a linking compound or compounds. At least two reactions are usually involved in one of which the hapten and linking compound are chemically coupled together and in the other of which the carrier and linking compound are coupled. There may be additional steps involving for example the coupling together of two linking compounds. It is usually desirable to couple a substantial plurality of haptens to a single carrier molecule.

Spector U.S. Pat. No. 3,766,162 discloses a radioimmunoassay for barbituric acids using antibodies generated by synthetic antigens, the subject of the patent. The antigen comprises a barbituric acid hapten coupled to a protein carrier. The barbituric acid has a 5-substituent and is coupled to the carrier by a peptide bond to that substituent. Spector reports, col. 5, ines 41–43, that the antibody will not differentiate between barbituric acids having different subsituents in the 5 position.

Miyadera et al. report in the Journal of Medicinal Chemistry (1971) vol. 14 No. 9 pp. 873-8 introduction of an alkylene group at the 3-position of the barbituric acid and coupling to a maleimide using a tosyloxy compound. The conjugate is used as an in vivo probe and is apparently not antigenic. Preparation of antibodies and immunoassays are not contemplated.

BRIEF DESCRIPTION OF THE INVENTION

This invention provides an antigen for raising an antibody useful to assay for the presence in samples, especially in an animal body fluid sample, of a physiologically significant barbituric acid target of formula:

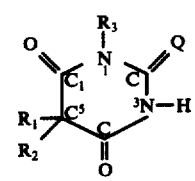

(1)

where Q is selected from the class consisting of O and S: $R_1$ has from 1 to 3 carbon atoms and is selected from the class consisting of saturated and unsaturated hydrocarbon groups, monohalo substituted hydrocarbon groups, ether groups and thoether groups; $R_2$ is selected from the class consisting of a phenyl group and saturated and unsaturated hydrocarbon groups containing from 1 to 6 carbon atoms; and $R_3$ is selected from the class consisting of H and $CH_3$.

For raising antibody binding with a corresponding, and thus providing a means for assaying for, barbituric acid, this invention provides an antigen, comprising a hapten coupled by a linking agent residue to a carrier, of the following formula:

(2)

-continued

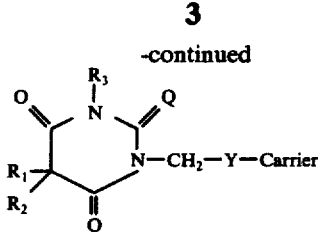

Q, $R_1$, $R_2$ and $R_3$ are as above and $—CH_2 — Y —$ is a residue from a linking agent which has been coupled to the hapten and to the carrier, and Y comprises a member selected from the class consisting of a direct bond, saturated and unsaturated straight and branched chain alkylene groups having from 1 to 6 carbon atoms and aromatic groups having from 6 to 14 carbon atoms. The carrier is a macromolecule which confers antigenicity.

The invention comprises hapten-protein conjugates where the hapten comprises barbital, phenobarbital, propallylonal hexobarbital, secobarbital and methitural bonded at one of the nitrogen atoms to a linking agent residue. The linking agent residue may include ethylene amide or ethylene phenylaza groups.

The antigen may be described as a hapten-carrier conjugate. The hapten is the part of the molecule closely resembling the target and this is coupled through the linking agent to the carrier. It is preferred that a plurality of haptens is so coupled to a single carrier to provide a three-dimensional molecule having an outer periphery of haptens.

The antigens of this invention generally have a hapten identical to the barbituric acid target except that a methylene group is coupled at the 3-nitrogen. The selection of this coupling position and the presence of the methylene group are important features of this invention. They are significant not just from a chemical viewpoint, but also from an immunological and from a physiological viewpoint.

Physiologically, it is desirable for the assay to be able to distinguish between individual barbiturates because they have different activities. This imposes a heavy burden on the immunology because it implies that the antibody used in the assay must be sufficiently specific to bind with the desired target barbiturate but not with others. More practically this means that the antibody's affinity for or binding constant with the target barbiturate should be much greater than with others, and should preferably be two or three orders of magnitude greater.

Surprisingly the antibodies of this invention, raised to the antigens of this invention can provide good and useful assay results. This is because of two factors, the recognition and use of which constitute important features of the present invention.

One factor is that, because of the presence of the 3-N-methylene group in the antigen, the antibody can be expected to bind with the corresponding 3-N-methyl substituted barbituric acid as well as with the corresponding barbituric acid which does not have a methyl substituent in the 3 position but is substituted at that position only by hydrogen. This multiple binding possibility should be unattractive from a physiological point of view. However, it is acceptable because of the second factor which is tthat the 3 N-methyl unsubstituted barbituric acids and the 3 N-methyl substituted barbituric acids have comparable physiological activity.

It will be noted that in both the target formula and the antigen formula $R_3$ can be hydrogen or methyl.

In most cases the antigen for a particular target will have a hapten identical to the target except for a methylene group in the 3 position of the hapten and a hydrogen group in the 3 position of the target. However, because of the dual binding character of the antibody, where $R_3$ is methyl in the target, it can be, and preferably is, hydrogen in the antigen.

No preferred use is presently contemplated for the antigen where $R_3$ is methyl. However, it is expected that its antibody will have utility in binding with its corresponding target, as well as with otherwise corresponding targets where none of, one or the other of, or both of the nitrogens are methyl substituted.

In considering the foregoing it should be noted that rotation of the barbituric acids about the 2-5 axis renders the 1 and 3 positions sterically equivalent, except when the two nitrogens have different substituents and the two 5 substituents are different.

The present invention also provides a process for preparing a synthetic antigen which is a barbiturate hapten coupled to a carrier as in formula (2) above. The process comprises the steps of reacting a carrier, which confers antigenicity, with a barbituric acid of formula:

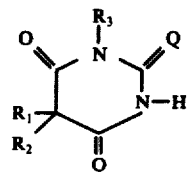

where Q, $R_1$, $R_2$ and $R_3$ are as in formula (1) above, with a linking agent of formula selected from the class consisting of $Z—CH_2—R_4—X_1$ and $CH_2=CH—X_2$ where Z is a leaving group displacable in a substitution reaction; $R_4$ is selected from the class consisting of a direct bond, saturated and unsaturated straight and branched chain alkylene groups having from 1 to 6 carbon atoms and aromatic groups having from 6 to 14 carbon atoms; and $X_1$ and $X_2$ each include a moiety that can be directly coupled to the carrier, with $X_2$ being an electron withdrawing group, whereby in the reaction the methylene group is substituted into the barbituric acid with a direct bond to the nitrogen atom in the 3 position.

DETAILED DESCRIPTION OF SOME PREFERRED EMBODIMENTS OF THE INVENTION

The following are some examples of target barbiturate compounds of interest:

Barbital

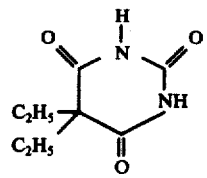

where $R_1$ and $R_2$ are both ethyl; and $R_3$ is hydrogen;

Phenobarbital

-continued

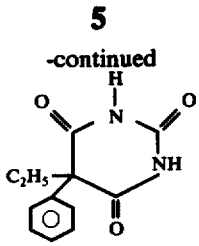

where $R_1$ is ethyl, $R_2$ is phenyl and $R_3$ is hydrogen;

Propallylonal

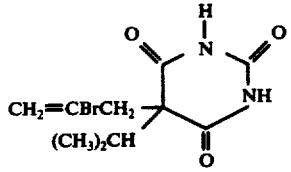

where $R_1$ is 2-bromoallyl, $R_2$ is isopropyl and $R_3$ is hydrogen;

Hexobarbital

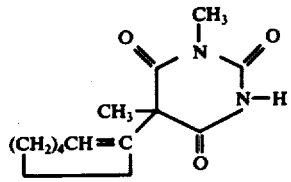

where $R_1$ is methyl and $R_2$ is 1-cyclohexen-1-yl; and $R_3$ is methyl;

Secobarbital

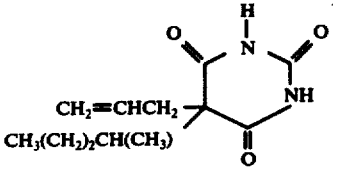

where $R_1$ is alkyl, $R_2$ is 1-methylbutyl and $R_3$ is hydrogen; and

Methitural

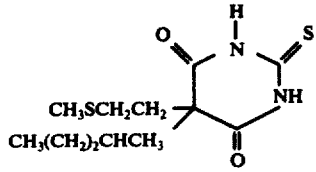

where $R_1$ is 2-(methylthio)-ethyl, $R_2$ is 1-methylbutyl and $R_3$ is hydrogen.

Others include amobarbital, pentobarbital, butabarbital and thiopental.

Where $R_3$ is methyl and where $R_2$ is different from $R_1$ the target compound will be optically active. However, there appears to be no significant differential biological acitivity between the isomers so that the optical activity of these compounds is therefore ignored for the purpose of the present invention, and the racemates are used. The separated isomers could of course be used individually.

$R_2$ can be aromatic, e.g. phenyl; straight-chain aliphatic e.g. ethyl; or branched-chain aliphatic, e.g. n-butyl or n-hexyl; cyclic, e.g. cyclohexen-1-yl; and saturated or unsaturated ethylenically, e.g. allyl or acetylenically, e.g. 1-methyl-2-pentenyl.

In the antigen, Y is preferably a direct bond or a methylene, ethylene or propylene group, or if aromatic, phenylene or naphthalene.

Referring to the linking agent, $Z-CH_2-R_3-X_1$, its leaving group moiety Z can be, for example, chloro, bromo, or iodo, with bromo preferred. It can also be a quaternary ammonium group provided the adjacent methylene carbon atom is not sterically hindered. However, a preferred group is a tosyloxy group, —OTs, where Ts is a tosylate group, that is, a p-toluene sulfonate ester.

Many reactions are known for coupling to a carrier and can be used in the present invention. The particular nature of X will depend upon what coupling groups are available on the carrier and which coupling reaction is to be used as well as upon its compatibility with the conditions for substituting the barbiturate.

Two convenient coupling reactions are carbodiimide condensation and diazotization. In carbodiimide condensation an amine group is reacted with a carboxyl group to form an amide bond or bridge. Natural proteins commonly have both groups available and accordingly $X_1$ can conveniently be amino or carboxyl. Diazotization is a useful route where the carrier has available diazotizable aromatic rings, in which case $X_1$ should be aminophenyl.

In some cases, it may be desirable for $X_1$ to be blocked during the reaction with the barbiturate and unblocked for coupling to the carrier. For example where $X_1$ is amino, $NH_2$, it can be blocked with a phthalimide, acetyl or trifluoroacetyl group.

The $CH_2=CH-X_2$ linking agent couples to the barbiturate in a reaction known as a Michael addition reaction. This agent constitutes an attacking nucleophile and reacts to produce an intermediate of formula:

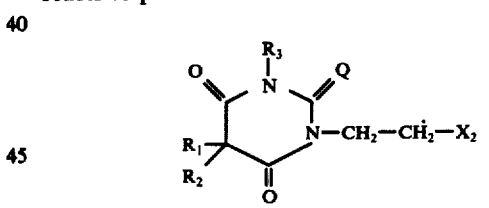

$X_2$ can be —CHO, —CN, —CO.OC$_2$H$_5$, —CO.O.CH$_3$, —CO.CH$_3$ or —CO.C$_2$H$_5$.

Alkaline hydrolysis or oxidation of these compounds yields corresponding carboxylic acid which can readily be coupled to a carrier having available amino groups, such as a protein, by carbodiimide condensation.

The reaction sequence can be either direct or a reverse coupling sequence. In the direct sequence the linking agent is first coupled to the barbituric acid hapten, and then preferably a plurality of linking-agent-substituted haptens is coupled to the carrier by reaction with the linking agent group $X_1$ or $X_2$. In the reverse coupling sequence, the latter step is effected first, that is to say, preferably a plurality of linking agent molecules is coupled to a carrier and then a hapten molecule is coupled to each linking agent.

For a direct sequence, Z and $X_1$ must be such that if $X_1$ is also an attacking nucleophile, Z will leave the linking agent more readily than X, so that undesired coupling mechanisms are avoided. With reverse coupling this need not necessarily be the case although care will be needed to ensure that the Z group does not enter into the carrier-coupling reaction.

It has been noted that sterically, the two nitrogen atoms of the barbituric acid are equivalent when $R_3$ is —H. Little if any of the di-N-substituted compound is formed in the reaction but, if necessary can be separated by chromatogrophy.

Preferably the barbituric acid used for synthesizing the antigen is used in the form of its salt, for example, the sodium or potassium salt, or for solubility in organic solvents a quaternary ammonium salt such as te tetramethyl. This salt may have to be synthesized, which can be done without difficulty.

One way of preparing the tetramethyl ammonium salt is by reacting tetramethylammonium hydroxide with the barbituric acid in methanol and evaporating to dryness:

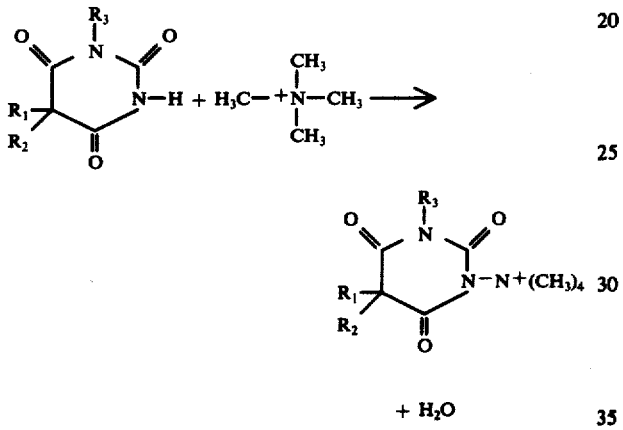

Similarly, where $X_1$ is tosylate it may be necessary to synthesize the linking agent. This can be done using the reactive tosylate halide, e.g. the chloride. In a preferred embodiment of the invention the linking aent is 2-hydroxy ethyl Phthalimide tosylate which can be prepared by reacting para-tosylate chloride with 2-hydroxy ethyl phthalimide suspended in pyridine at a reduced temperature and precipitating the product in ice water:

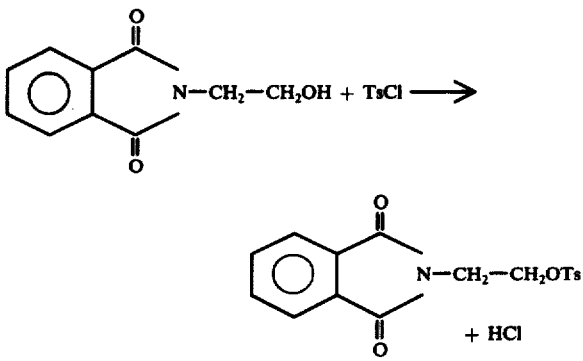

This reagent is a useful starting material since after reaction with the barbiturate the phthalimide moiety can be converted to an amino group by reaction with hydrazine hydrate, for example by refluxing in 95% ethanol. The N-amino ethyl barbiturate can then readily be coupled through the amino group to an available carboxyl group on a proteinic carrier, by carbodiimide condensation. Prior to such coupling the N-amino ethyl barbiturate should be purified for example by chromatography. Reaction of the $Z-CH_2-R_4-X_1$, linking agent, for example the phthalimidyl tosylate described above, with the barbituric acid or barbiturate salt can be carried out in an organic solvent at an elevated temperature. The solvent can be polar, e.g. dimethyl formamide (DMF), and the temperature will be such as to optimize the reaction without destroying the reactant or boiling the solvent. With DMF the temperature can be from 100° to 140° C with 120° C preferred. Equimolar proportions are preferred.

Conveniently the barbiturate salt is dissolved in the solvent with stirring and then the linking agent in added and stirring continued to completion which may take several hours, e.g. about 1 to 4 hours. The desired N-substituted barbituric acid can be recovered by pouring the reaction mixture into ice water and extraction with an organic solvent such as chloroform. The extract can then be chromatographed to give the desired product.

The Michael addition reaction is also effected in a polar organic solvent, e.g. tetrahydrofuran (THF), with stirring from 2 to 6 hours at a temperature of from 50° to 100° C preferably about ° C. Preferably about equimolar proportions of the barbiturate salt and linking agent $CH_2=CH-X_2$ are used, and the solvent should be anhydrous. The desired omega-substituted -N-ethyl barbituric acid can be recovered by pouring the reaction mixture into ice water, extraction with an organic solvent and chromatographic isolation and purification, as above.

The omega substituent, $X_2$, can then be used as a reactive site for coupling to a carrier. Conveniently, $X_2$ is first hydrolyzed to a carboxyl. Where the carrier has available amine groups coupling can then be effected by carbodiimide condensation, or dehydration, with formation of a peptide bond.

Hydrolysis can be effected in alkaline aqueous-ethanolic solution. This is convenient where $X_2$ is an ester moiety.

In order to be capable of conferring antigenicity, the carrier will normally be anitgenic itself, although it may be an incomplete anitgen, becoming complete only when coupled to the hapten. To be antigenic, the carrier must be an immunogenic substance, that term being used to refer to a substance capable of eliciting production of antibodies in a host animal to which the immunogenic substance is administered. While, in general, it is believed that the terms "carrier" and "immunogenic substances" are clearly understood in the art, and the discussion herein is not meant to modify the ordinary significance of the terms, further definition is provided here for a clearer understanding of the development.

The animal to which the antigenic substance is administered must be one having an effective immunological system. The immunogenic substances must be "foreign" to the animal, in the sense of not being "self". That is, the immunogenic substance administered must not be one which is a natural body substance of the animal and would, therefore, be accordingly tolerated by the animal's immunological system.

Generally, the antibodies elicited upon injection of the immunogenic substance into the animal will be generated by the host animal and will be capable of reacting or binding with the anitgen in an observable and selective way. Thus, the antibodies will display some degree of discrimination between the administered immunogenic substance and other immunogenic materials.

The requirements for immunogenicity are not fully understood. However, it appears that for a molecule to be antigenic, it must have a certain complexity and a certain minimal molecular weight. Formerly, it was thought that the lower molecular weight limit to confer antigenicity was about 5,000. However, antigenicity has recently been demonstrated with molecules having molecular weights as low as 2,000. Molecular weights of 3,000 and more appear to be more realistic as a lower limit for immunogenicity, and approximately 6,000 or more is preferred.

Exemplary immunogenic carrier materials are those set forth in Cremer et al., "Methods in Immunology" (1963), W. A. Benjamin Inc., New York, pages 65 to 113. That disclosure is herein incorporated by reference. The carrier material can be a natural or synthetic substance, provided that it is an antigen or a partial antigen. For example, the carrier material can be a protein, a glycoprotein, a nucleoprotein, a polypeptide, a polysaccharide, a lipopolysaccharide, or a polyaminoacid. An example of an apparently incomplete antigen is the polypeptide glucagon.

A preferred class of natural carrier materials is the proteins. Proteins can be expected to have a molecular weight in excess of 5,000, commonly in the range of from 34,000 to 5,000,000. Specific examples of such natural proteins are bovine serum albumin (BSA), keyhole limpet hemocyanin (KLH), human immunogammaglobulin (HGG), and thyroglobulin.

Exemplary of the synthetic carrier is a polyaminoacid, polylysine. Where the synthetic antigen comprises a partially antigenic carrier conjugated with a hapten, it will generally be desirable for the conjugate to have a molecular weight in excess of 6,000, although somewhat lower molecular weights may be useful.

Preferably, the natural carrier has some solubility in water or aqueous alcohol. Also preferably, the synthetic antigen is water soluble. Desirably, the carriers are nontoxic to the animals to be used for generating antibodies.

The carrier must have a, or preferably a plurality of, functional moieties by means of which it can be coupled. Of course, these groups can be introduced synthetically. Preferably, in practicing the present invention, a single carrier moiety should have a plurality of hapten moieties coupled to it, for example, from about 10 to about 70. In general, the maximum possible number of haptenic moieties per carrier molecule is preferred. Subject to steric hindrance, the maximum number will be determined by the number of reactive coupling groups on the carrier. For example, with BSA, it appears that the maximum number of haptenic moieties that can be coupled is between 60 and 70.

In preparing the antigens of the invention it is, as a practical matter, very desirable to obtain them with a high degree of purity. High antigen purity appears to be an important requisite for optimum antibody production. Accordingly, it is desirable for the process to provide for isolation of the antigen from antigenically distinct materials. The latter will normally be undesired large molecules that may confuse the immune response of animals used for producing antibodies. A feature of the process of the invention is that it is designed to minimize the formation of such undesired antigenically distinct materials.

Removal of small molecule reactants and reaction products is generally desirable, particularly if they are likely to couple to the carrier. However, some small molecule substances may be useful, for example for pH control. Thus a convenient end-product form in which to recover the antigen is in a buffered aqueous solution which is suitable for direct administration to animals.

The process of the invention can accordingly include a number of purification steps using well-known techniques such as column chromatography, dialysis and recrystallization. Further it will be generally desirable to use high purity reactants. For a natural protein carrier commercially available high purity fractions are desirable. In general, the hapten containing material should be as pure as possible for the carrier coupling step.

Antibodies can be raised by administration of an antigen of the invention to vertebrate animals, especially mammals such as goats or rabbits, using known immunization procedures. Usually a buffered solution of the antigen accompanied by Freund's adjuvant is injected sub-cutaneously at multiple sites. A number of such administrations as intervals of days or week is usually necessary. A number of animals, for example from three to twenty, is so treated with the expectation that only a small proportion will produce good antibodies. However, one goat producing high quality antibodies can provide sufficient for several hundred thousand assays. The antibody is recovered from the animals after some weeks or months.

If desired the recovered antibodies can be purified. This can be done by absorbing the antibody on an insoluble matrix to which the target or the precursor antigen is secured so that the desired antibody binds with the target or antigen and is retained. The antibody can be recovered by elution for example with an acetic acid or urea solution.

However, if the best techniques are employed throughout, it is possible that antibody purification may not be necessary.

Antibodies so produced are useful in assays for the presence of their respective targets in a liquid sample, particularly a body fluid sample, notably blood or urine, or alternatively saliva or tissue extracts.

The assay, according to the present invention, is an immunochemical method of assaying for the presence of a target according to the present invention, that target being contained in a sample. The method employs an antibody obtained by the immunologic response of a vertebrate animal to administration of an antigen according to the present invention, and the antibody is specific to the target. Further, the assay employs a standard, the standard and target competitively binding with the antibody to form an antibody-standard complex and an antibody-target complex. The antibody-standard complex has an artificially introduced radiation label so that the complex can be assayed quantitatively by measurement of the radiation emanating from it. In order for the method to be properly employed, the affinities of the antibody for the standard and for the target must be known quantitatively. In employing the method, a known quantity of the sample and a known quantity of the standard are allowed to compete for binding with a known quantity of the antibody. The radiation emanating from the antibody-standard complex so formed is determined so that the quantity of antibody-bound standard can be calculated and the quantity of target in the sample can be deduced. This deduction is carried out by attributing any difference between the quantity of bound standard determined and the quantity expected, based on the known binding characteristics of the antibody, to binding of the antibody with the target.

In one embodiment of the assaying procedure, the introduced label is radioactive and the antibody-standard is separated from any non-complexed, labeled material after allowing competition binding and before determination of the radiation emanated.

In another embodiment of the assaying method, the introduced label is fluorescent and the standard is provided with a chemical moiety giving it a fluorescence spectrum overlapping the natural fluorescence spectrum of the antibody. The complex can then be assayed by measurement of the perturbation of the antibody fluorescence due to binding with the standard.

The standard is a substance known to bind with the antibody and can be, for example, the target, the antigen used to raise the antibody, or the hapten used to make the antigen. Similarly, it can be a similar antigen having the same hapten bound to a different carrier, but at the same position on the hapten. Conveniently, where the radiation constitutes radioactive emission, such as beta or gamma rays, the standard can carry the radioactive label in the form of a radioactive isotope, e.g., tritium, $I^{125}$, or $C^{14}$, although, as an alternative, the antibody can be labeled. The standard can also be a close homolog of the hapten on the target.

When the separation of the complex from the unreacted standard is necessary, as is normally the case with radioactive labeling, this can be effected by phase separation, insolubilizing of one of the components to be separated, etc. Thus, with a labeled antibody, the use of an antigenic standard having a plurality of antibody binding sites can cause the antibody-standard complex to precipitate while, if the target is a small molecule, the antibody-target complex will remain in solution. Alternatively, the antibody can be insolubilized, as described elsewhere in the specification, and the standard labeled, so that unreacted standard stays in solution and can easily be separated from the complex.

One example of such a separation is the addition of saturated ammonium sulfate to the complexed mixture. The mixture, with the added ammonium sulfate, is then centrifuged which results in deposition of most of the protein, including the antibody-standard complex. The antibody-standard complex can then be removed as a solid and measurement carried out on this solid. Alternatively, the uncomplexed liquid standard is subjected to measurement of radiation emanation.

A further possibility is to absorb the standard with dextran-charcoal, after allowing for competition binding, and to then make the scintillation count for radiation on the liquid phase containing the antibody-standard complex following separation of the solid phase which contains the unreacted standard. In this case, the standard is labeled and is a small molecule, especially a radioactive isotope labeled target molecule.

While the count for radiation is normally made upon the antibody-standard complex, as this is either more convenient or is believed to reduce experimental error, it will be clear that where there is a separation of unbound, labeled material from the antibody-standard complex, the determination of the radiation emanating from the antibody-standard complex can equally well be made by measuring the radiation emanating from the unreacted, labeled material. From this measurement, the difference from the known amount of labeled material added can be calculated.

The term "radiation" is used in an ordinary dictionary sense and refers to energetic emissions originating from individual atoms or molecules which are generally attributed to internal changes within the atom or molecule. These emissions are in contrast to physical phenomena, such as, for example, precipitations which are the result of the inter-molecular or inter-atomic effects, and may require a large-scale cooperation of a great number of atoms or molecules to be meaningfully expressed. Radiation is significant for immunoassays as it provides a means of remotely monitoring the behavior of very small quantities of matter.

Thus, in addition to energetic emissions, radiation includes such phenomena as fluorescence and electron spin resonance. Fluorescence usually requires excitation by exposure to ultraviolet light, but the product is radiation. Thus, energy, usually in the form of light, is emitted as a result of intra-molecular change.

Where fluorescence is the form of radiation measured, it is feasible for the assay to be conducted without any separation of materials. Thus, antibodies, which are naturally fluorescent, have an absorption spectrum and an emission spectrum. If the standard chosen is a molecule having, as a label, a chemical group which fluoresces in spectra overlapping the antibody, then, when the standard complexes with the antibody, the natural fluorescence of the antibody is perturbed by that of the standard, and this perturbation can be measured. When the emission spectrum of the standard overlaps the absorption spectrum of the antibody, fluorescence enhancement will be observed from the complex at the antibody emission wavelength, and when the absorption spectrum of the standard overlaps the emission spectrum of the antibody, fluorescence quenching will be observed from the complex at the antibody emission wavelength. Comparable effects can be displayed using polarization perturbation.

Electron spin resonance labeled assays can also be conducted without the need for separation. A paramagnetic labeling group, such as a nitroxide group, is attached, for example, to the standard. When subjected to a microwave frequency magnetic field, an electron spin resonance spectrometer can detect distinct resonance peaks characteristic of the nitroxide ring label. When the standard combines with antibody, these peaks are substantially extinguished, providing a direct indication of the degree of binding.

In order that those skilled in the art may be better enabled to practice the invention, the following examples are given. These should be considered as exemplary only, and not as limiting in any way the full scope of the invention as covered in the appended claims.

EXAMPLE 1 a. Synthesis of N-tetra methyl ammonium diethyl barbiturate 45.3 gm (0.25 mole) of tetramethyl ammonium hydroxide is added to 46 gm. of 5,5-diethyl barbituric acid (0.25 mole) in 200 ml. of methanol and the solution is evaporated to dryness. The residue is recrystallized from methanol to yield 49.0 gm. of colorless crystals with a melting point of 227° to 228° C. The yield is 76.2%.

b. Synthesis of 2-hydroxyethylphthalimide tosylate 1.62 gm. of 2-hydroxyethylphthalimide (8.5 millimoles) is suspended in 35 ml. of pyridine and treated with 5.6 gm. of p-tosylyl chloride (29.4 milli-moles) for 3 hours at 0–5° C. The reaction mixture is poured into ice water, the precipitate is collected, washed with water, dried and purified by recrystallization or column chromatography to yield the desired tosylate c. Synthesis of 1-[2-(phthalimidyl) ethyl]-5,5-diethyl barbituric acid 1.54 gm. of the tetramethyl ammonium barbiturate (6.0 milli-moles) from (a) is dissolved in 25 ml. of DMF at 120° C with stirring. 2.1 gm. of the phthalimidyl tosylate (6.1 milli-moles from (b) is added and the reaction mixture is stirred for 2 hours at 120° C. It is poured into ice water and extracted with chloroform. The extract is chromatographed to yield the desired product.

d. Hydrolysis to 1-(aminoethyl)-5,5-diethyl barbituric acid 100 mg. of the phthalimidyl derivative from (c) is dissolved in 10 ml. of 95% ethanol containing 0.02 ml. hydrazine hydrate and the solution is refluxed for 2 hours. The solvent is removed under reduced pressure and the aminoethyl barbiturate is purified by chromatography.

e. Carrier coupling 500 mg. of bovine serum albumin (BSA) is dissolved in 20 ml. of water. To it is added a solution or solution/suspension of 50 mg. of 1-(aminoethyl)-5,5-diethyl barbituric acid from (d) in 5 ml. of water and the pH is adjusted to 3.9 to 4.1. 60 mg. of water soluble carbodiimide is added and the mixture is stored for 6 to 8 hours at 4° C. The solution is then transferred to dialysis tubing and dialysed against 6 liters of 0–1N HCL at a pH of 1–2. The dialysis solution is changed after two days, and dialysis continued for a further two days. It is then dialysed against 0.1M phosphate buffer at pH 7.5.

EXAMPLE 2 a. Synthesis of 1-(2-carbethoxyethyl)-5,5-diethyl barbituric acid (Michael Addition Reaction)

1.54 gm. of the tetra methyl ammonium barbiturate (6.0 milli-moles) from (a) is dissolved in anhydrous THF at 70° C with stirring. 0.6 gm. of ethyl acrylate (6.0 milli-moles) is added and the reaction mixture is refluxed for a further 4 hours at 70° C with stirring. It is poured into ice water extracted with chloroform and the desired product isolated by chromatography.

The thus-isolated ethyl ester is hydrolyzed in alkaline aqueous-ethanolic solution to give the desired acid. This is effected by using a caustic soda and stirring overnight at room temperature.

Coupling to BSA and purification is then effected in the manner of Example (e) except that the pH during coupling and the first two dialysis steps is maintained between 8 and 9.

EXAMPLE 3

Examples 1 and 2 are successively repeated using equivalent amounts of keyhole limpet hemocyanin, human immunogammaglobulin and thyroglobulin in place of bovine serum albumin. Equivalent results are obtained.

EXAMPLE 4

Examples 1 to 3 are successively repeated using equivalent amounts of phenobarbital, propallylonal, hexobarbital, secobarbital, methitural and amobarbital, pentobarbital, butabarbital, and thiopental in place of the 5,5 diethyl barbituric aid. Equivalent results are obtained.

Raising of Antibodies

Approximately 2 mg. doses of antigen in 0.1% aqueous solution with Freund's adjuvant are injected at multiple, subcutaneous sites in rabbits. The injections are repeated at intervals according to known immunization procedure. The rabbits are bled at intervals and the anti serum is collected and used without purification.

Radioimmune Assay

The radioimmune assay is performed by incubating various dilutions of antisera obtain from animal bleedings, with tritiated target compound (the respective barbituric acid) in the presence of buffer 4° C. After two hours a neutral, saturated ammonium sulfate solution is added. The resultant precipitates are sedimented by centrifugation at 3,000 rpm for 15 minutes at 4° C and the supernates are decanted off. Aliquots of 0.5 ml. water and 10 ml. Aquasol are counted for labeled target. The addition of increasing amounts of unlabeled target to a fixed amount of labeled target and antiserum results in a competitive inhibition of the labeled target bound to antibody.

This enables a standard curve for the antibody to be established showing the variation of inhibition of binding with concentration.

The specificity of the antibody is then determined by allowing for competitive binding of known concentrations of the antibody with known concentrations of the labeled standard and successive potential cross-reactants. The cross-reactivity is defined according to the method of Abraham as the relative quantity of target to cross-reactant that produces 50% inhibition multiplied by 100 for percentage.

If desired, the antibodies of this invention can be insolubilized, or otherwise supported, on a solid matrix. Examples of materials to which the antibody can be attached are glass, synthetic polymers, synthetic resins, and cellulose. The material to which the antibody is attached or otherwise insolubilized can have an extensive, continuous form, such as a sheet, or it can be in the form of discrete particles of desired size. The antibody can be secured to the material in a number of ways.

Among the methods for attaching or otherwise insolubilizing the antibody to a solid matrix are covalent bonding, van der Waal's forces, hydrogen bonding, etc. Thus, the methods for attaching the antibody to the solid matrix are relatively weak intermolecular forces, covalent bonds, or the adsorptive forces attributable to a porous surface. An example of van der Waal's forces occurs with the adhesion of an antibody to a predominantly hydrophobic plastic surface, such as a polyolefin. Apparently, there is hydrophobic bonding to the hydrophobic amino acid residues to the antibody.

Some of the methods for bonding of the antibody to a solid matrix are discussed in Weliky and Weetall, *Immunochemistry*, Vol. 2, pages 293–322 (1965).

Another method for conveniently covalently bonding the antibody to a solid is by diazotizing available amino groups on the antibody into available, activated, aromatic rings on the solid material.

It may be desirable to modify the material, particularly for the purpose of securing the antibody to it. Thus, for covalent bonding, carbodiimide condensation, with the formation of an amide bond between the antibody and the material, can be used. For this purpose, the material should have available primary, non-aromatic amine groups or carboxyl groups to couple with, respectively, available carboxyl or amino groups on the antibody. An amino glass suitable for this purpose is known. Suitable synthetic resins or polymers may be available, in addition, or existing resins can be modified. Similarly, many derivatized celluloses are known, and cellulose can, in general, be provided with appropriate groups.

In attaching the antibody to the substrate material, it is normally desirable to ensure that the active binding site of the antibody remains available and accessible. This can be facilitated by blocking the site before coupling to the support material, and unblocking thereafter. Blocking can be conveniently effected by complexing the antibody with the hapten for which it is specific and deblocking can be effected with an eluting agent, for example, acetic acid or urea.

For sorption on a porous surface, another method for insolubilizing the antibody on a solid matrix, it is desirable for the pore size of the material, e.g., porous particles, to be selected for optimum accommodation of the antibody.

In the body, drugs are frequently metabolized, often to reduce their lipid solubility to make them more readily excretable through the kidneys. Some examples of the sort of metabolic reactions that can occur are oxidation of aliphatic side chains to the corresponding alcohol; desulfuration, or the replacement of sulfur by oxygen for example in thiopental; and N- demethylation.

The latter process might account for the similar activity of the N-methyl substituted and unsubstituted barbituric acids. These in vivo processes are discussed in Goldstein et al. "Principles of Drug Action" (2nd. Ed. 1974) John Wiley & Sons, pp. 245 et seq.

Depending upon the particular clinical circumstances, it may accordingly be desirable to assay for the metabolite. For this purpose antibody to the metabolite can be prepared by the methods described herein from an antigen synthesized by using the appropriate metabolite as a hapten in place of the barbituric acid. Where the metabolite has reactive group, e.g. a carboxyl or an amino, it may be necessary to block it during carrier coupling.

Where desulfuration is a relevant metabolic process (for example in the case where pentobarbital is a metabolite of thiopental), it will be noted that antibody to the oxygenated barbituric acid can be used to assay for the presence of that acid whether directly administered or present as the metabolite of the thio barbituric acid.

EXAMPLE 5

Examples 1 & 2 are successively repeated using equivalent amounts of 5-hydroxyethyl-5'-ethyl barbituric acid, and 5-ethyl-5-(3'-hydroxy-1'-methylbutyl) barbituric acid in place of the diethyl barbituric acid. Equivalent results are obtained. Antibodies raised from the antigens produced are useful in assaying for the hydroxylated metabolites of, respectively, barbital and pentobarbital.

What is claimed is:

1. A synthetic antigen comprising a hapten coupled to a carrier which has the following formula:

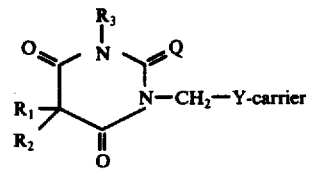

where Q is selected from the class consisting of O and S; $R_1$ has from 1 to 3 carbon atoms and is selected from the class consisting of saturated and unsaturated hydrocarbon groups, monohalo substituted hydrocarbon groups, ether groups, thioether groups; $R_2$ is selected from the class consisting of hydrocarbon groups containing from 1 to 6 carbon atoms; $R_3$ is selected from the class consisting of H and $CH_3$; $-CH_2-Y-$ is a residue from a linking agent which has been coupled to the hapten and to the carrier and Y comprises a member selected from the class consisting of a direct bond, saturated and unsaturated straight and branched chain alkylene groups having from 1 to 6 carbon atoms and aromatic groups having from 6 to 14 carbon atoms; and the carrier is macromolecule which confers antigenicity.

2. A synthetic antigen defined by claim 1 but wherein a plurality of the haptens are coupled to a single carrier in the manner shown in claim 1.

3. The synthetic antigen of claim 2 wherein the hapten is phenobarbital.

4. The synthetic antigen of claim 2 wherein the hapten is 5,5 diethyl barbituric acid.

5. The synthetic antigen of claim 2 wherein the hapten is selected from the class consisting of propallylonal, hexobarbital, secobarbital and methitural.

6. The synthetic antigen of claim 2 wherein Y comprises a second methylene group coupled to the shown methylene group and a residue coupled to the carrier of a group selected from the class consisting of an amide group and a phenylazo group.

7. The synthetic antigen of claim 2 wherein the carrier is a natural protein.

8. The synthetic antigen of claim 7 wherein the protein carrier is selected from the class consisting of bovine serum albumin, keyhole limpet hemocyanin, human immunogammaglobulin and thyroglobulin.

9. A synthetic antigen comprising a plurality of identical haptens coupled to a protein carrier by a linking agent residue through the three position nitrogen atom of the hapten, wherein the hapten is selected from the class consisting of barbital, phenobarbital, propallylonal, hexobarbital, secobarbital and methitural and the linking agent is selected from the class consisting of methyleneamide and ethylenephenylazo, the ethylene portion of the residue being bonded to the nitrogen atom.

10. Protein-amidoethylene-N,5,5-phenylethyl barbituric acid.

11. Antibody raised by, directed to and binding with the antigen of claim 2.

12. Antibody raised by, directed to and binding with the antigen of claim 9.

13. Antibody raised by, directed to and binding with the antigen of claim 10.

14. A process of preparing a synthetic antigen which is a barbiturate hapten coupled to a carrier which confers antigenicity which comprises the steps of reacting a barbituric acid of formula:

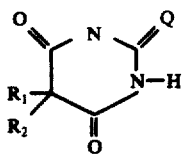

where Q is selected from the class consisting of O and S; $R_1$ has from 1 to 3 carbon atoms and is selected from the class consisting of saturated and unsaturated hydrocarbon groups, monohalo substituted hydrocarbon groups, ether groups, tioether groups; $R_2$ is selected from the class consisting of hydrocarbon groups containing from 1 to 6 carbon atoms; and $R_3$ is selected from the class consisting of H and $CH_3$; with a linking agent of a formula selected from the class consisting of $Z-CH_2-R_4-X_1$ and $CH_2=CH-X_2$, where Z is a leaving group displaceable in a substitution reaction, $R_4$ is selected from the class consisting of a direct bond, saturated and unsaturated straight and branched chain alkylene groups having from 1 to 6 carbon atoms and aromatic groups having from 6 to 14 carbon atoms, and $X_1$ and $X_2$ each include a moiety that can be directly coupled to the carrier, with $X_2$ being an electron withdrawing group, whereby in the reaction Z in the linking agent is substituted into the barbituric acid with a direct bond to the nitrogen atom in the three position; and the step of coupling the product of the foregoing reaction to a carrier through said moiety.

15. The process of claim 14 wherein Z is a tosylate group.

16. The process of claim 14 wherein the $Z-CH_2-R_4-X_1$ linking agent is 2-hydroxyethylphthalimide tosylate.

17. The process of claim 14 wherein the linking agent is ethylacrylate.

18. The process of claim 14 wherein the linking agent is $Ch_2=CH-X_2$ and, after reaction of the hapten and the linking agent, $X_2$ is hydrolyzed to a carboxyl group and coupled to a proteinic carrier through a carbodiimide condensation by formation of an amide bond between said carboxyl group and an amino group on the carrier.

19. The process of claim 16 wherein, after reaction between the hapten and the linking agent, the phthalimide moiety is hydrolyzed to an amino group and coupled to a proteinic carrier through a carbodiimide condensation by formation of an amide bond between said amino group and available carboxyl group on the carrier.

20. An immunochemical method of assaying for the presence in a sample of a barbiturate hapten target as defined in claim 1, wherein said method employs an antibody obtained by the immunologic response of a vertebrate animal to administration of an antigen according to claim 1 and wherein said antibody is specific to the target, said method also employing a standard, the antibody binding with the target to form an antibody-target complex and competitively binding with the standard to form an antibody-standard complex, the antibody-standard complex having an artificially introduced radiation label enabling the complex to be assayed quantitatively by measurement of radiation emanating from it, the affinities of the antibody for the standard and for the target being known quantitatively, said method comprising allowing a known quantity of the sample and a known quantity of the standard to compete for binding with a known quantity of the antibody and determining the radiation emanating from the antibody-standard complex, thereby enabling the quantity of antibody-bound standard to be calculated and the quantity of target in the sample to be deduced.

21. The method of claim 20 wherein the label is radioactive and the antibody-standard complex is separated from any non-complexed labeled material after allowing competition binding and before determination of the emanated radiation.

22. The method of claim 20 wherein the label is fluorescent and the standard is provided with a chemical moiety giving it a fluorescence spectrum overlapping the natural fluorescence spectrum of the antibody, whereby the complex can be assayed by measurement of the perturbation of the antibody fluoroescence due to its binding with the standard.

23. The antibody of claim 11 insolubilized by securing it to a solid matrix.

24. A synthetic antigen defined by claim 1 but wherein the hapten is a metabolite of the hapten defined by said claim.

25. Antibody raised by, directed to and binding with the antigen of claim 24.

* * * * *